(12) United States Patent
Lim et al.

(10) Patent No.: US 7,749,259 B2
(45) Date of Patent: Jul. 6, 2010

(54) SLOTTED SCREW FOR USE WITH A VERTEBRAL MEMBER

(75) Inventors: Roy K Lim, Germantown, TN (US); Michael C. Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 160 days.

(21) Appl. No.: 11/102,395

(22) Filed: Apr. 8, 2005

(65) Prior Publication Data

US 2006/0241623 A1    Oct. 26, 2006

(51) Int. Cl.
*A61B 17/86* (2006.01)

(52) U.S. Cl. ...................................... 606/314

(58) Field of Classification Search ............. 606/72–73, 606/300–321, 232; 411/372.5, 373, 387.7, 411/387.8, 395, 403, 404, 418–421, 451.4, 411/479
See application file for complete search history.

(56) References Cited

U.S. PATENT DOCUMENTS

| | | | | |
|---|---|---|---|---|
| 4,712,957 | A * | 12/1987 | Edwards et al. ............ 411/82.1 |
| 4,872,840 | A | 10/1989 | Bori |
| 4,944,759 | A | 7/1990 | Mallory et al. |
| 5,007,931 | A | 4/1991 | Smith |
| 5,338,197 | A | 8/1994 | Kwan |
| 5,484,437 | A * | 1/1996 | Michelson .................... 606/61 |
| 5,632,748 | A * | 5/1997 | Beck et al. .................... 606/89 |
| 5,725,581 | A | 3/1998 | Bränemark |
| 5,735,898 | A | 4/1998 | Bränemark |
| 5,766,263 | A | 6/1998 | Grundei et al. |
| 5,769,852 | A * | 6/1998 | Brånemark ................... 606/65 |
| 5,941,882 | A | 8/1999 | Jammet et al. |
| 6,015,410 | A * | 1/2000 | Tormala et al. ............. 606/232 |
| 6,129,763 | A * | 10/2000 | Chauvin et al. ........... 623/17.11 |
| 6,290,711 | B1 * | 9/2001 | Caspari et al. .............. 606/232 |
| 6,371,989 | B1 * | 4/2002 | Chauvin et al. .......... 623/17.11 |
| 6,508,830 | B2 * | 1/2003 | Steiner ........................ 606/232 |
| 6,520,963 | B1 * | 2/2003 | McKinley .................... 606/266 |
| 6,540,748 | B2 * | 4/2003 | Lombardo .................... 606/61 |
| 6,610,099 | B1 | 8/2003 | Albrektsson et al. |
| 6,755,835 | B2 | 6/2004 | Schultheiss et al. |
| 7,044,953 | B2 * | 5/2006 | Capanni ........................ 606/73 |
| 2001/0007074 | A1 * | 7/2001 | Strobel et al. .................. 606/73 |
| 2002/0038123 | A1 * | 3/2002 | Visotsky et al. ............... 606/73 |
| 2002/0123752 | A1 | 9/2002 | Schultheiss et al. |
| 2004/0220575 | A1 * | 11/2004 | Biedermann et al. .......... 606/73 |
| 2005/0021036 | A1 * | 1/2005 | Whitmore et al. ............. 606/73 |

FOREIGN PATENT DOCUMENTS

DE    10319781 B3 *  8/2004
EP    0622058 A2    11/1994

* cited by examiner

*Primary Examiner*—Eduardo C Robert
*Assistant Examiner*—Tara R George

(57) ABSTRACT

A screw for use with vertebral members having one or more slots that extend along at least a section of the length. The slots are sized to contain bone growth material. A portion of the screw length may also include threads to assist in inserting and anchoring the screw into a vertebral member. In use, the bone growth material is loaded into one or more of the slots. Once loaded, the screw may be inserted into the vertebral member to a predetermined depth. At this depth, the slots deliver the bone growth material to a position to allow for bone growth to occur.

17 Claims, 3 Drawing Sheets

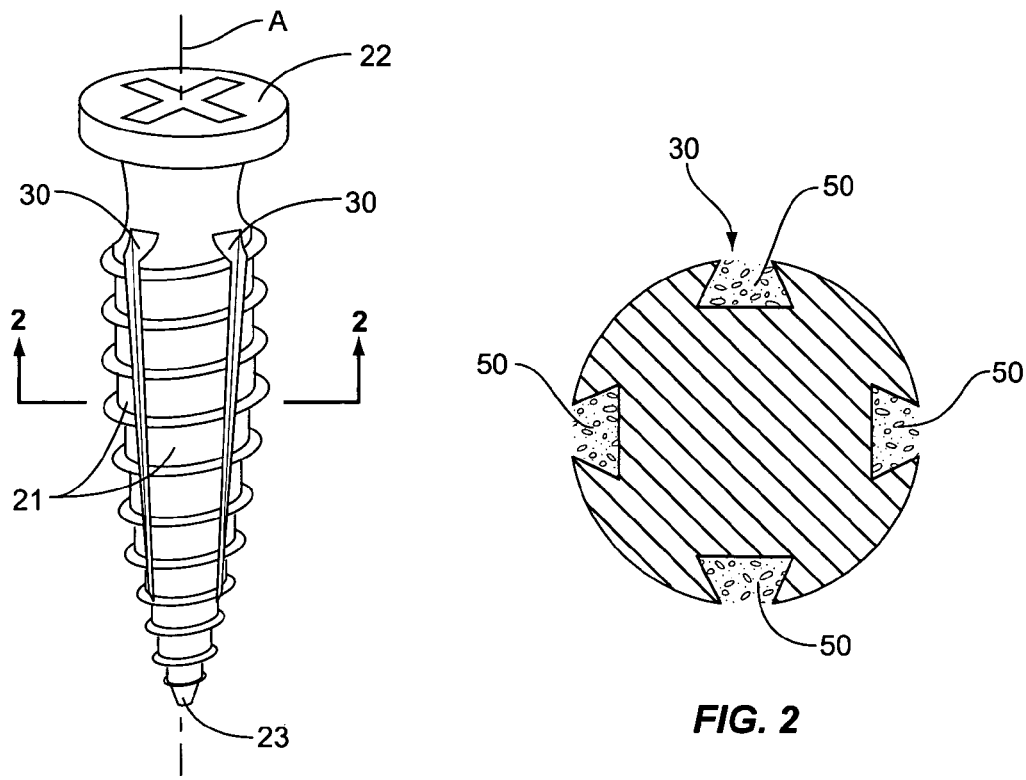
FIG. 1
FIG. 2
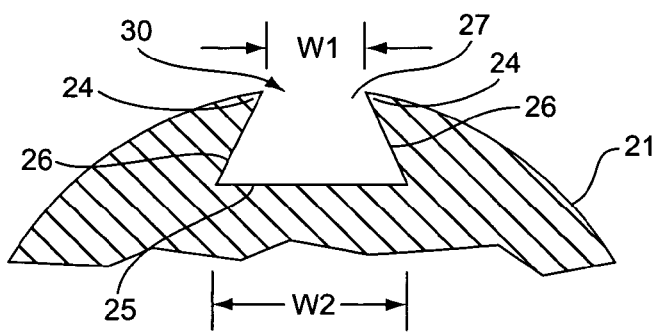
FIG. 3
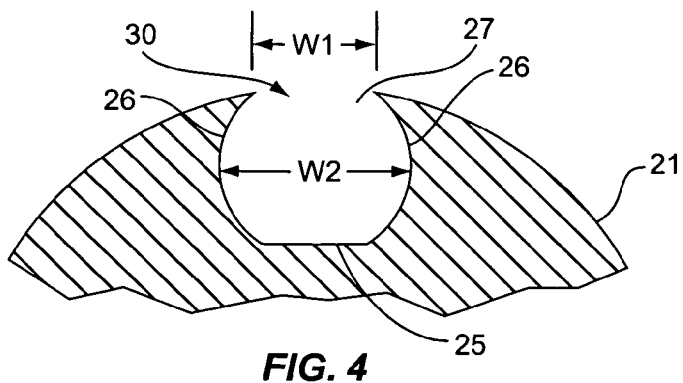
FIG. 4

SLOTTED SCREW FOR USE WITH A VERTEBRAL MEMBER

BACKGROUND

Screws are used in various settings for attachment to vertebral members. The screws may be used to attach together the vertebral member, or may be used to attach a support device, such as a vertebral rod. In one specific embodiment, screws are attached to the pedicle. One issue with previous screws is that the interface between the thread and the bone experiences stresses immediately following installation. This is especially seen in the thread-to-cancellous bone interface. The thread interface may tend to slip or move after installation, thus inhibiting bone adhesion and bone growth.

Bone growth materials have been used to promote bone growth. One application is the use of bone growth materials to facilitate attachment of a vertebral member to an intervertebral device, such as an intervertebral spacer. The bone growth material is delivered with the spacer and positioned in a manner to promote growth with the vertebral member. However, screws have been unable to adequately carry the bone growth material to the desired location within the vertebral member.

SUMMARY

The present invention is directed to embodiments of a screw for use with vertebral members. The screw may include one or more slots that extend along at least a section of the length. The slots are sized to contain bone growth material. A portion of the screw length may also include threads to assist in inserting and anchoring the screw into a vertebral member.

One method of using the screw may include loading one or more of the slots with bone growth material prior to insertion. Once loaded, the screw can be inserted into the vertebral member. The threads assist in moving the screw into the vertebral member to a predetermined distance. At this predetermined position, the slots deliver the bone growth material to allow for bone growth to occur.

BRIEF DESCRIPTION OF THE DRAWINGS

FIG. 1 is a perspective view of a screw according to one embodiment of the present invention;

FIG. 2 is a cross-section view of the screw cut along line 2-2 of FIG. 1;

FIG. 3 is a is a partial cross-section view of the slot according to one embodiment of the present invention;

FIG. 4 is a partial cross-section view of the slot according to one embodiment of the present invention;

DETAILED DESCRIPTION

Figure 5:
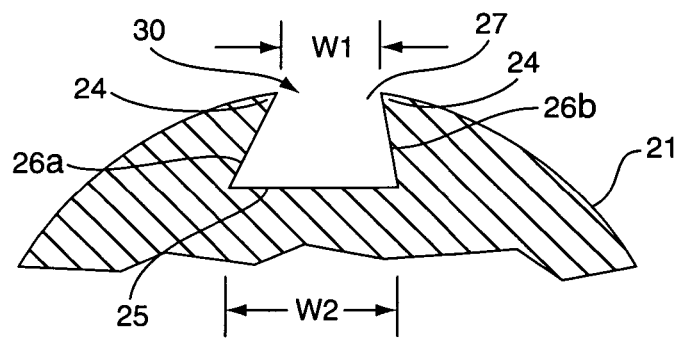
FIG. 5 is a partial cross-section view of the slot according to one embodiment of the present invention.

The present invention is directed to embodiments of a screw for use with vertebral members. The bone screw 10 includes a body 20 that may be at least partially threaded for insertion into a vertebral member 99. One or more slots 30 are positioned along the body 20. The slots 30 may include a retaining feature sized to contain bone growth material 50. Once installed, the bone growth material 50 within the slots 30 is positioned to facilitate bone growth and securely attach the screw 10 within the vertebral member 99.

FIG. 1 illustrates one embodiment of a screw body 20 having a head 22 at a proximal end and a tip 23 at a distal end. Threads 21 extend along at least a portion of the body between the head 22 and tip 23. In this embodiment, the threads 21 are positioned in central and distal sections of the body 20. A plurality of slots 30 are positioned within the body 20 and sized to receive bone growth material 40. The slots 30 extend into the body 20 a distance from the threaded exterior.

In this embodiment, each slot 30 includes an interior wall 25 formed by a central section of the body 20. Each of the slots 30 further includes a pair of opposing sidewalls 26 spaced a predetermined distance apart and forming an exterior opening 27. The embodiment illustrated in FIGS. 1 and 2 illustrate four separate slots 30 evenly spaced around the periphery of the body 20. The body 20 may include various numbers of slots 30 which may be spaced at a variety of spacings and having a variety of orientations. The screw body 20 has a substantially circular cross-sectional shape.

FIG. 3 illustrates a schematic view of one slot embodiment. The slot 30 includes an interior wall 25, and opposing sidewalls 26. An exterior opening 27 leads into the slot 30. The area of the slot 30 is sized to contain a predetermined amount of bone growth material 40. In this embodiment, each of the sidewalls 26 is substantially linear and sloped inward towards the exterior opening 27. The top sections of the sidewalls 26, adjacent to the opening 27, form retaining features 24 that hold the bone growth material 50 within the opening. A width W1 of the exterior opening 27 is smaller than the maximum extent of interior width W2. In this embodiment, the maximum width is at the interior wall 25. The reduced width at the exterior opening 27 maintains the bone growth material 40 within the slot 30 as the screw 10 is being inserted into the vertebral member 99. If the opening 27 were larger, bone growth material 40 may escape from the slot 30.

FIG. 4 illustrates another embodiment of a slot 30 having arcuate sidewalls 26. The bottom of the slot 30 is formed by the interior wall 25 and an external opening 27 is positioned along the threaded surface 21. The arcuate surfaces of the sidewalls 26 result in the maximum width W2 being within a middle depth of the slot 30. The external opening 27 has a width W1 that is smaller than the maximum width W2. As with the embodiment of FIG. 3, the top section of the sidewalls 26 adjacent to the opening 27 form retaining features for maintaining the bone growth material 50 within the slot 30.

FIG. 5 illustrates another embodiment of the slot 30 having non-symmetrical first and second sidewalls 26a, 26b. The width W1 at the exterior opening 27 is less than the maximum width W2 that, in this embodiment, is at the maximum depth.

Figure 6:
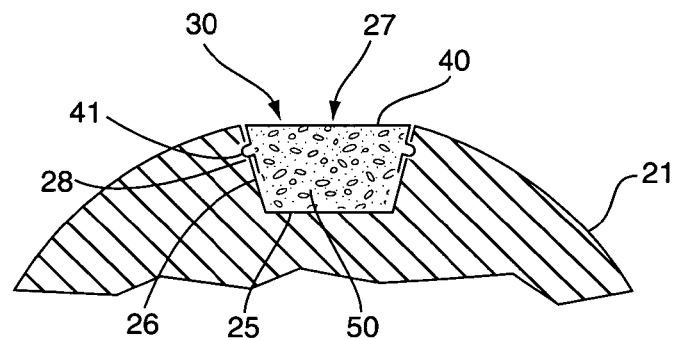
FIG. 6 is a partial cross-section view of the slot with a cap according to one embodiment of the present invention.

FIG. 6 illustrates another embodiment of the slot 30 having a cap 40 forming a retaining feature to maintain the bone growth material 50 within the slot 30. The cap 40 is constructed of a material that allows for the bone growth material 50 to grow between the screw body 20 and vertebral member 99. The cap 40 may be positioned inward from an outer edge of the slot 30 to prevent inadvertent removal during screw insertion. Examples of cap materials include hydroxyapatite, bone morphogenic proteins, sponge, and porous metallic material.

Cap 40 may include a pair of extensions 41 that are placed within receivers 28 in the sidewalls 26. The cap 40 is flexible allowing for the extensions 41 to be moved inward to mount within the receivers 28. The natural outward bias of the extensions 41 is than adequate to maintain the cap 40 attached to the screw body. The bone growth material 50 is positioned within the slot 30 beneath the cap 40 during insertion into the vertebral member 50.

Figure 7:
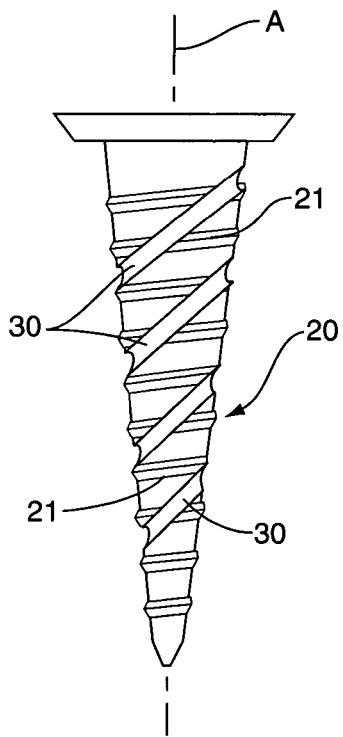
FIG. 7 is a side view of a screw according to one embodiment of the present invention.
Figure 8:
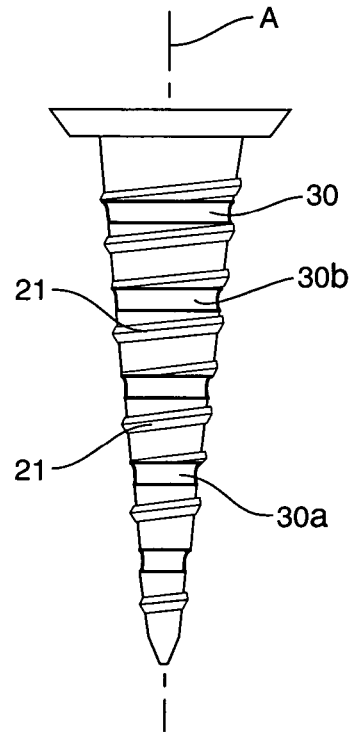
FIG. 8 is a side view of a screw according to one embodiment of the present invention.

The slots 30 may be oriented on the screw body 20 in a manner of different orientations. As previously discussed in FIG. 1, slots 30 are aligned in a vertical direction that extend substantially along a longitudinal axis A that runs the length of the screw body 20. FIG. 7 illustrates another embodiment with a single slot 30 that helically winds about the screw body 20. The helical slot 30 may have a variety of pitches and helical directions, depending upon the application. Threaded sections 21 are positioned about the slot 30 to assist in anchoring the screw 10 to the vertebral member 99. FIG. 8 illustrates an embodiment with a plurality of slots 30 arranged in a horizontal manner. The spacing between the slots 30, and the number of slots 30 may again vary depending upon the application. Threaded sections 21 are again positioned between the slots 30. The slots 30 in FIGS. 7 and 8 each substantially encircle the longitudinal axis A, as opposed to the slot of FIG. 1 that extends substantially along the axis. Embodiments may also include combinations of different slot arrangements, such as both horizontal and vertical slots 30. In another embodiment, a first section of the screw includes a first slot arrangement, and a second section includes a different, second slot arrangement.

The threads 21 are positioned on the exterior of the screw body 20 to assist in inserting the screw into the vertebral member 99 and anchoring the screw 10. The threads 21 may be continuous along the exterior surface but for being interrupted by the slots 30. In one specific embodiment such as that illustrated in FIG. 1, a single thread 21 extends around the screw body 20 as is interrupted by the slots 30. In another embodiment, each threaded section may have a separate thread pitch. The thread 21 may extend the entire length of the body 21 from the head 22 to the tip 23, or a distance less than the entire length.

The slots 30 may have a variety of depths and widths depending upon the application. The depth and width is adequate to contain a predetermined amount of bone growth material 50. Further, the depths and widths of different slots 30 may vary. By way of example using the FIG. 8, a first slot 30a may have a first depth and width that are different than the second slot 30b.

The term "bone growth material" used here means virtually any osteo-conductive and/or osteo-inductive material that promotes bone growth or healing, including natural, synthetic and recombinant proteins, hormones, and the like. The bone growth materials used may comprise a therapeutically effective amount of a bone inductive factor such as a bone morphogenic protein in a pharmaceutically acceptable carrier. Examples of factors include recombinant human bone morphogenic proteins (rhBMPs) rhBMP-2, rhBMP-4 and heterodimers thereof. However, any bone morphogenic protein is contemplated, including bone morphogenic proteins designated as BMP-1 through BMP-13, which are available from Genetics Institute, Inc., Cambridge, Mass. Various osteoinductive factors are contemplated whether obtained as above or isolated from bone.

The bone growth material 50 may include a demineralized bone matrix and, optionally, a carrier, such as a gelatin substance. The demineralized bone matrix can be provided in the form of a powder, paste or gel. When provided as a powder, the osteogenic material can be reconstituted with sterile water, saline, glycerin or other physiological solutions. The reconstituted material is molded and inserted into the slots 30. An osteogenic material can be applied to the screw 10 by the surgeon during surgery or the screw 10 may be supplied with the composition pre-applied. In such cases, the osteogenic composition may be stabilized for transport and storage. The osteogenic material can be provided as a putty that can be retained in and about the implant assembly. The osteogenic putty is a moldable, flowable material that sets up to a semi-rigid form at about body temperature. The intervertebral spacer with the osteogenic material is then inserted into a prepared disc space. The osteogenic material can also include a reinforcement component such as bone chips, preferably cortical bone chips. Examples of bone growth material suitable for use with this invention include, but are not limited to: OSTEOFIL, which is commercially available from Regeneration Technologies, Inc. of Alachua, Fla.; GRAFTON CRUNCH available from Osteotech of Eatontown, N.J. and ALLOMATRIX, available from Allosource of Denver, Colo.

Figure 9:
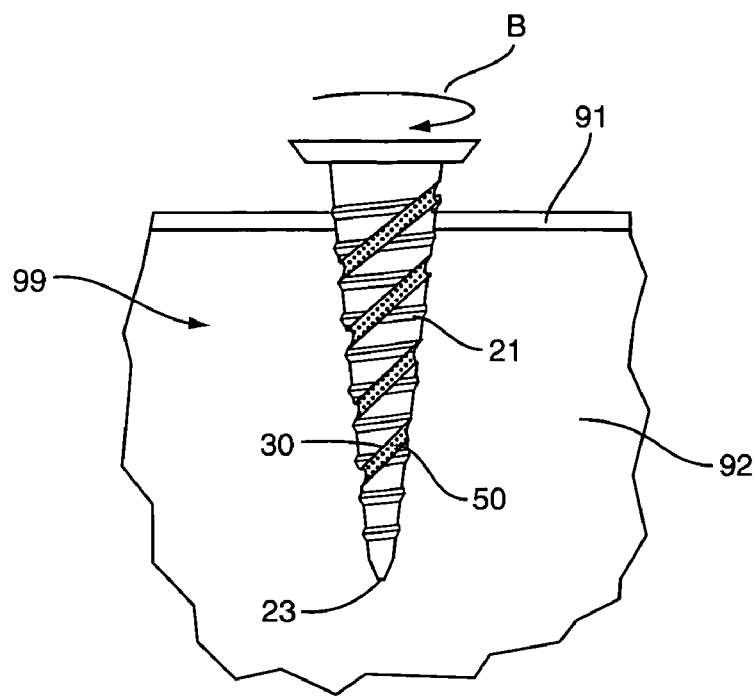
FIG. 9 is a side view of the screw being inserted into a vertebral member according to one embodiment of the present invention.
Figure 10:
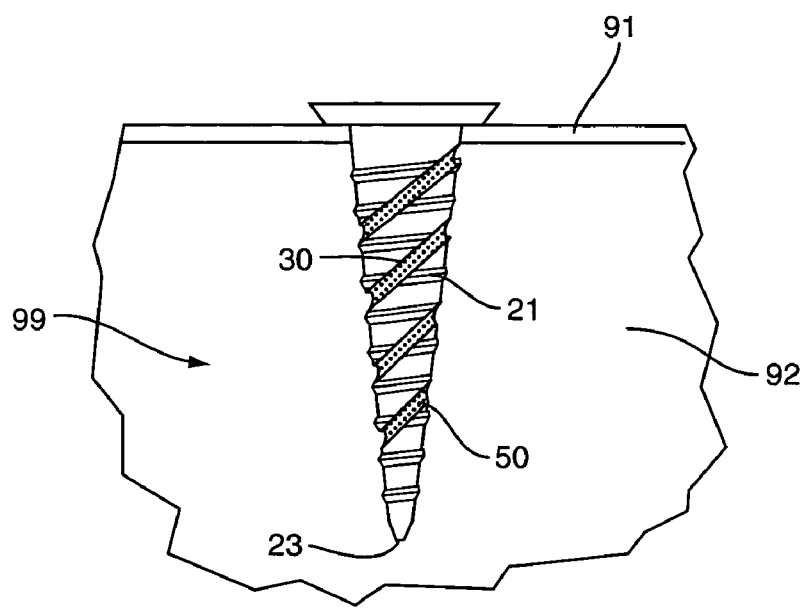
FIG. 10 is a side view of the screw inserted into the vertebral member according to one embodiment of the present invention.

FIGS. 9 and 10 illustrate on embodiment of inserting the screw into a vertebral member 99. Prior to insertion, an amount of bone growth material 50 is inserted into the slots 30. Bone growth material 50 may be placed within each of the slots 30, or within a limited number of slots 30. The screw 10 is than inserted into the vertebral member 99 as illustrated in FIG. 9. The pointed tip 23 and threads 21 ease the insertion through the hardened cortical section 91 and into the cancellous section 92 of the vertebral member 99. The screw is inserted through rotations in the directions of arrow B. The retaining features of the slots 30 eliminate and/or reduce escape of the bone growth material 50 during rotation. FIG. 10 illustrates the screw 10 fully inserted into the vertebral member 99. The slots 30 with bone growth material 50 are positioned within the vertebral member 99 to allow for bone growth to more fully attach the screw 10. To further facilitate bone growth, the slots 30 may have roughened surfaces. This facilitates the connection of the bone growth material 50 between the screw 10 and vertebral member 99.

The present invention may be carried out in other specific ways than those herein set forth without departing from the scope and essential characteristics of the invention. In one embodiment, the central section of the body 20 is solid. In another embodiment, a portion or all of the central section is porous. In the embodiments of FIGS. 3 and 4, each of the sidewalls 26 has a similar shape. Other embodiments may include one sidewall 26 having a first shape (e.g., linear), and the second sidewall 26 having a second shape (e.g., arcuate). The screw 10 may be constructed from a variety of materials, including titanium, surgical grade stainless steel, or other bio-compatible material using fabricating techniques known in the art. The present embodiments are, therefore, to be considered in all respects as illustrative and not restrictive, and all changes coming within the meaning and equivalency range of the appended claims are intended to be embraced therein.

What is claimed is:

1. A screw for use with a vertebral member comprising:
an elongated body extending between a distal end and a proximal end and having an external thread, the elongated body including a longitudinal axis that extends through the distal and proximal ends; and a plurality of circumferential slots spaced apart along the longitudinal axis between the proximal and distal ends, each of the slots extending radially inward from an exterior surface towards the longitudinal axis, the each slot having an exterior opening with a first width, and a maximum slot width within an interior section radially inward from the exterior opening, the each slot including a bottom wall and an exterior opening with the bottom wall being in closer proximity to the longitudinal axis than the exterior opening;

the slots extend into the body where the body includes a solid interior at the longitudinal axis.

2. The screw of claim 1, wherein the external thread extends between the distal end and the proximal end of the elongated body.

3. The screw of claim 1, wherein a cross-sectional shape of the each slot is symmetrical.

4. The screw of claim 1, further comprising a plurality of caps wherein each cap extends over only one respective slot to contain a bone growth material within said plurality of slots.

5. A screw for use with a vertebral member comprising:
an elongated body having an external threaded section on an exterior surface of the body; and
at least one slot extending lengthwise along the body and across the threaded section and having a first sidewall and a second sidewall and an interior wall positioned radially inward from an opening of the slot, at least one of the sidewalls having a retaining feature that extends into the slot forming a reduced opening having an uncompressed width that is less than an interior width of the slot, the at least one slot extending radially inward from the exterior surface into the elongated body a depth that is less than a diameter of the elongated body;
wherein a width of the slot radially inward from the retaining feature is greater than at the retaining feature.

6. The screw of claim 5, wherein the first and second sidewalls are each substantially linear.

7. The screw of claim 5, wherein the slot extends along the elongated body in a substantially vertical orientation.

8. The screw of claim 5, wherein the elongated body has a longitudinal axis and the slot encircles the longitudinal axis.

9. The screw of claim 5, wherein the retaining feature is integral with the elongated body.

10. The screw of claim 5, wherein one of the first and second sidewalls is substantially arcuate.

11. The screw of claim 5, further comprising a cap that extends over the slot and encloses the slot.

12. A screw for use with a vertebral member comprising:
an elongated body having a longitudinal axis; and
a slot extending along the elongated body and having a first sidewall and a second sidewall and an interior wall radially inward from an opening of the slot, at least one of the sidewalls having a retaining feature that extends into the slot forming a reduced opening having a width that is less than an interior width of the slot, the slot extending radially inward from an exterior surface into the elongated body; and
a cap that extends over the slot.

13. The screw of claim 12, wherein the slot encircles the longitudinal axis.

14. A screw for use with a vertebral member comprising:
an elongated body with a length measured between top and bottom ends and a lateral section that extends between the ends, the elongated body having an external threaded section that extends along the lateral section and a longitudinal axis, the elongated body including a solid interior along the longitudinal axis; and
a slot extending lengthwise along the lateral section and cutting into and across the threaded section and interrupting threads along the lateral section, the slot having an exterior opening with a first width and having a maximum slot width within an interior section of the slot radially inward from the exterior opening, the slot including a bottom wall; and
a cap sized to attach to the elongated body, to be disposed at least partially within the slot, and to enclose an interior section of the slot.

15. The screw of claim 14, wherein the cap is positioned within the slot inward from an outer edge of the elongated body to prevent inadvertent removal during insertion into the vertebral member.

16. The screw of claim 14, wherein the slot comprises sidewalls that each include a receiver into which the cap is mounted to maintain attachment of the cap.

17. The device of claim 14, wherein the slot is substantially linear.

\* \* \* \* \*